(12) United States Patent
Daniels et al.

(10) Patent No.: US 6,250,465 B1
(45) Date of Patent: Jun. 26, 2001

(54) SHARPS CONTAINER

(75) Inventors: Dan Daniels, Dandenong South (AU); Philip David Savory, Mornington (NZ); Mario Matkovich, Williamstown (AU)

(73) Assignee: Catalina Nominees Pty. Ltd., Dandenong South (AU)

(*) Notice: Subject to any disclaimer, the term of this patent is extended or adjusted under 35 U.S.C. 154(b) by 0 days.

(21) Appl. No.: 09/463,045
(22) PCT Filed: May 14, 1999
(86) PCT No.: PCT/AU99/00360
    § 371 Date: Jan. 13, 2000
    § 102(e) Date: Jan. 13, 2000
(87) PCT Pub. No.: WO99/59659
    PCT Pub. Date: Nov. 25, 1999

(30) Foreign Application Priority Data

May 15, 1998 (AU) .................................................. PP3533

(51) Int. Cl.$^7$ .................................................. B65D 83/10
(52) U.S. Cl. ............................................. 206/370; 206/366
(58) Field of Search ..................................... 206/366, 363, 206/370, 742, 743, 744; 220/908

(56) References Cited

U.S. PATENT DOCUMENTS

| | | |
|---|---|---|
| 4,715,498 | 12/1987 | Hanifl . |
| 5,065,939 | 11/1991 | Boothe et al. . |
| 5,076,429 | 12/1991 | Patrick et al. . |
| 5,154,345 | 10/1992 | Shillington . |
| 5,387,735 | 2/1995 | Ponsi et al. . |
| 5,413,243 | * 5/1995 | Bemis et al. ................ 220/908 |
| 5,947,285 | * 9/1999 | Gaba et al. ................ 206/366 |

FOREIGN PATENT DOCUMENTS

| | | |
|---|---|---|
| 0 842 641 A1 | 5/1998 | (EP) . |
| WO 96/31414 | 10/1996 | (WO) . |

* cited by examiner

Primary Examiner—David T. Fidei
(74) Attorney, Agent, or Firm—Lyon & Lyon LLP

(57) ABSTRACT

A sharps container for receiving and storing medical sharps and waste materials which prevents hand access to within the container and has a wide access opening. The container (10) comprises a receptacle (11) having an opening which is closable toy a hinged lid (24) which is movable between opened and closed positions. A pivotal tray (16) is mounted at the opening wherein for the opened position of the lid (24) the tray (16) has a rest position at which it is accessible for medical sharps and waste materials to be placed thereon. The tray (16) is then pivotally moveable for disposal of the medical sharps and waste materials therefrom into the receptacle. The tray (16) is arranged such that as it pivots a front edge thereof moves towards the opened lid (24), and a rear edge (23) thereof moves closely adjacent a guard (35), wherein the rear edge (23) clears the guard (35) for disposal of medical sharps and waste materials into the receptacle from the tray (16) when the front edge of the tray is proximate the lid (24), thereby preventing hand access to within the receptacle (11) for all positions of the tray (16) about its pivotal axis. The tray (16) is biased to return to its rest position. The lid (24) and tray (16) are operatively associated such that as the lid is opened from a closed position, the tray (16) is moved from a storage position within the receptacle (11) to its rest position. The tray (16) is foldable to facilitate its storage within the receptacle (11) upon closing the lid (24).

30 Claims, 6 Drawing Sheets

SHARPS CONTAINER

TECHNICAL FIELD

The present invention relates to a container for use in the disposal of medical and hospital sharps such as needles, syringes, surgical blades and the like and associated medical or other waste materials. In particular, the invention relates to a secure reusable sharps container for location in a medical clinic, hospital etc and into which medical sharps and waste materials can be placed for storage pending later disposal or destruction of that material at an appropriate facility for that purpose.

BACKGROUND

Hospitals and medical clinics use many sharps objects that are disposed of rather than cleaned and reused. Generally it is desirable and often necessary to provide secure containers into which the sharps objects and waste materials are placed for storage pending their disposal. These containers provide security against pilfering of used syringes and the like to prevent them falling into the hands of intravenous drug users or others who are likely to use them without proper sterilization. Such containers are also designed so that when sharps are placed therein, they are safely stored without placing hospital staff and patients at risk of contact with the sharps, which otherwise could result in needle stick injuries and the potential for transfer of infectious disease.

Sharps containers are known and examples of such containers are shown in the following specifications; U.S. Pat. No. 4,715,498, U.S. Pat. No. 5,103,997, U.S. Pat. No. 5,178,322, and EP 90313126.6, all of which disclose disposable containers. Reusable containers are also known, as shown for example by U.S. Pat. No. 5,413,243. A general problem with both disposable and reusable containers is that it is difficult to provide a container that has a large access opening and at the same time ensure prevention of hand access to within the container.

DISCLOSURE OF THE INVENTION

An object of the present invention is to provide a sharps container, which may be either disposable or reusable, having a high level of security against access to within the container. A subsidiary object is to provide a reusable sharps container construction which allows for embodiments of the container to have a large access opening.

According to the invention, there is provided a container comprising a receptacle for receiving and storing medical sharps and waste materials, the receptacle having an opening, a closure for dosing the opening, the closure being hinged to the receptacle for movement between opened and closed positions, a pivotal disposing means mounted at the opening wherein for the opened position of the closure, the disposing means is accessible for medical sharps and waste materials to be placed thereon, the disposing means being pivotally moveable for disposal of the medical sharps and waste materials therefrom into the receptacle, wherein the disposing means is arranged relative to the closure in its opened position, and the receptacle, to prevent hand access into the receptacle for all positions of the disposing means about its pivotal axis.

Preferably the pivotal disposing means is a tray which is biased to return to a rest position for the opened position of the closure, which is preferably a lid, wherein it is accessible for medical sharps and waste materials to be placed thereon. At its rest position, a front edge of the tray may be located adjacent to a front edge of the opening of the receptacle, with the closure being pivotally hinged to a rear edge of the receptacle opposite its front edge. With this construction, on pivoting of the tray, its front edge moves towards the opened closure, namely a lid, and its rear edge moves into the receptacle. This arrangement facilitates the provision of a wide access opening for disposal of medical sharps and waste materials into the receptacle in that the tray can provide a broad surface upon which the sharps and waste materials may be placed, which surface may be relatively widely spaced from the lid in its opened position, particularly a front edge thereof, depending upon the degree to which the lid is opened relative to the receptacle. Preferably the lid, at its opened position, extends at an angle of at least about 40° to the receptacle opening, which opening is typically the top of the receptacle.

Thus the closure in the form of a lid and the tray are arranged so that a gap exists between them and that gap is sufficient to allow sharps objects to be easily placed on the tray for subsequent disposal into the receptacle. The arrangement is such that pivotal movement of the tray upon placement of a sharps object thereon, causes a reduction in that gap so that as the tray rotates to a disposal position at which the interior of the receptacle is exposed, access to that interior is restricted by the reduced gap between the lid and the tray. That is, the tray, or a portion thereof, pivots in a direction towards the lid and the reduction in the gap therebetween is sufficient to prevent a user placing his/her hand therethrough to obtain access to within the receptacle. Preferably, the gap continues to be reduced as the tray pivots towards the lid and preferably the gap is substantially eliminated, or at least minimised at the point of disposal of the sharps object from the tray into the receptacle to prevent or effectively impede the fingers of a person disposing the sharps material from extending through the gap. It is preferable that the sharps material be deposited from the tray into the receptacle only upon pivoting of the tray to the extent that the gap is reduced the desired amount.

While both the tray and the lid may be arranged so that they limit access to within the receptacle, as discussed above, additional or alternative means may be provided to prevent access to within the receptacle when the container is being used. Such means may include guards or shields and these may be disposed to block gaps existing between various parts of the container, particularly such gaps that may be exposed during pivoting movement of the tray. In some arrangements the edges of the tray may be spaced away from other surfaces of the container, such as the internal receptacle walls, during its path of travel, so that access to within the receptacle might be gained at those points. Gaps may, for example, exist between an end or side of the tray and the adjacent receptacle wall, prior to or during pivotal movement of the tray to dispose of a sharps object. Thus, guards may be employed for example adjacent the or each end of the tray and may have a profile complimentary to the path of the ends, so that undesirable gaps permitting access to within the receptacle do not occur when the tray is either stationary or rotating.

While in the arrangement described above the lid is maintained in a generally stationary opened position throughout disposal of sharps material, an alternative arrangement is that the lid may be caused to pivot with the tray in order to reduce the gap between the lid and the tray for the reasons discussed above.

Preferably, the tray is foldable into a folded state as necessary for storage within the container and to facilitate closing of the container, or as a measure to save space when the container is closed. A foldable tray provides several advantages. One advantage resides in that such a tray can be provided in a size, in the unfolded state, that is convenient for a user of the container to easily deposit sharps material thereon, but in which state it would be inconvenient or difficult for the container to be closed if the tray were not foldable. Furthermore, the provision of a foldable tray enables a relatively large and easily accessible tray to be adopted, but that tray does not necessarily increase the overall bulk of the container particularly when the container is closed, given its foldable nature. Preferably the tray is accommodated within an upper portion of the receptacle, or within the lid that is provided to close the container, or partly within either. The provision of a foldable tray facilitates its accommodation in the container within such spaces and can minimise the reduction in sharps material storage space that may occur due to the requirement that the tray be located within the container in space that might otherwise accommodate waste sharps material.

Preferably the pivotal disposing means, whether or not in the form of a tray, extends outwardly of the container when at its rest position, to facilitate placement of sharps material thereon.

Preferably the lid and the pivotal disposing means are operatively associated such that the movement of the lid from its closed to its opened position moves the disposing means from an inoperative condition to an operative condition wherein it is accessible for medical sharps and waste materials to be placed thereon. In this embodiment of the invention, the pivotal disposing means may be a tray as described hereinabove, and the lid may include a depending arm and the receptacle a structure for engaging the arm, wherein the arm and the structure provide a stop arrangement which defines the opened position for the lid. The operative association of the tray and the lid may take any suitable form, but is preferably provided by a cam and follower arrangement, for example the arm of the lid may include a cam track and the tray may include a follower in the form of a pin engaged with the cam track. The pin may be disposed on a suitable portion of the tray, such as an edge portion, and engagement between the cam and follower may be permanent, or may occur only during a portion of the lid movement between its opened and closed positions. Other alternative arrangements may also be used, such as a linkage arrangement of struts, or a biasing arrangement in which movement of the lid permits a biasing force to act on the tray, or any combination of the above.

In this embodiment the tray may also be formed so as to be foldable, and be arranged to fold as necessary when the lid is closed. The tray may for example be arranged to fold as the lid is closed and to unfold as the lid is opened. Alternatively, the tray may be foldable independently of the lid and that folding may occur as a result of a separate action or mechanism undertaken or actuated manually prior to or during lid closure.

The invention anticipates the circumstance that the tray may not be folded each time the container lid is closed and the term "foldable" is used with respect to the tray to provide for such a circumstance. That is, folding of the tray may only occur when the container is filled beyond a certain level of sharps material in which there is insufficient space within the container to accommodate the tray in an unfolded state. In one form of the invention, the tray folds only upon engagement of a foldable portion of the tray with an upper level of sharps and waste materials in the receptacle. In this form of the invention, the extent to which the tray folds depends on the height of sharps and waste materials in the receptacle. Engagement of the tray with the sharps material serves as an indicator that the container is full, or is nearing its full capacity. Advantageously, the tray can be arranged to fold over itself through approximately 180° and can be arranged in that folded condition to extend across the opening of the receptacle, substantially transverse to the depth thereof in order to minimise the extent to which the tray extends into the receptacle in the folded condition. However, it is to be understood that complete folding of the tray through 180° may not always be necessary, unless the receptacle is substantially filled.

The position of the tray within the container when the lid has been closed preferably does not substantially reduce the amount of sharps material able to be disposed within the receptacle. The tray is therefore preferably stored in a manner in which projection thereof into the receptacle is negligible or minimised. Thus, the tray may be caused to overlie the sharps material disposed within the receptacle, and this is particularly appropriate if the tray is foldable. Alternatively, the tray may be caused to penetrate into the sharps material or waste within the receptacle, although this latter arrangement is not preferred as the sharps material or waste will generally tend to resist or impair that penetration. However the nature of the sharps material or waste may be such that the resistance to penetration may be insufficient to prevent closure of the lid.

In a further arrangement, movement of the tray may be to within a pocket formed, for example, within the receptacle, which pocket is not filled with sharps material. In still a further arrangement, the lid can accommodate at least a portion of the tray in the closed position. As can be understood from the above description a variety of options are available for accommodating the tray within the container.

The pivotal disposing means is preferably mounted so that placement of sharps material thereon causes pivoting movement thereof into a position in which the sharps material can be disposed into the receptacle. Moreover, the pivotal disposing means preferably returns to a rest position following pivoting movement to dispose of the sharps material. Pivoting movement of the disposing means to a disposal position may be arranged to occur under the weight of the sharps material placed thereon. Alternatively, the user of the container may urge the disposing means to pivot, such as by finger pressure, although equally, a different arrangement may be used to create pivoting movement. The first described arrangement is preferred, as an over-balance arrangement for the pivotal disposing means may be provided such that only a small load will cause pivoting movement. With this arrangement, after disposal of the sharps material into the receptacle, the pivotal disposing means will return under its over-balance to its rest position. An abutment can be provided to limit return pivoting movement of the pivotal disposing means to define its rest position and an edge of the receptacle opening may provide that abutment For a pivotal disposing means which is a tray, the tray in its rest position is preferably inclined toward the receptacle opening or into the receptacle, so that a sharps object placed onto the tray will tend to slide across it towards its lower rear edge from which the object is disposed into the receptacle. In the over-balance arrangement discussed above, tray inclination is advantageous, as sliding of the sharps object toward the lower edge promotes pivoting movement of the tray toward the disposal position, after which the tray will return under its over-balance to the rest position. If however, alternative means are employed to pivot the tray, return movement of the tray may be caused by any suitable means, such as biasing means.

An advantage of the invention resides in the manner in which the pivotal disposing means, for example a tray, can be presented for use in an open condition of the container. Advantageously, a forward portion of the tray extends beyond a front wall or surface of the receptacle and preferably also beyond the lid of the container. This protrusion of the tray beyond the receptacle and lid is such as to facilitate placement of a sharps object thereon without hindrance from the receptacle or lid.

Preferably the container includes a structure on which the pivotal disposing means is pivotally mounted, and this structure in turn is removably mounted on the receptacle and is moveable relative thereto for moving the pivotal disposing means away from the receptacle opening. In this embodiment, the lid is preferably moveable beyond its opened position to completely uncover the receptacle opening. Thus the lid and the pivotal disposing means may be moved, in turn, relative to the receptacle to leave Rs opening unobstructed such that the container can be emptied of its contents simply by inverting the receptacle. Preferably said structure is removably hinged to the receptacle opposite the hinged connection of the lid to the receptacle. This construction particularly facilitates automated handling of the container at a medical sharps and waste destruction facility in that the lid and the tray can be automatically moved to unobstructing positions relative to the e opening whilst remaining attached to the receptade, such that the receptacle can then be automatically inverted and thus emptied of its sharps and contaminated waste materials. Thus the invention allows for disposal of medical sharps and waste materials with increased safety in that the need for persons to handle the container at a destruction facility is minimised if not eliminated.

Preferably in this embodiment the pivotal disposing means is a tray, which may be biased to a rest position, may be foldable, may slope inwardly of the receptacle and which, in its rest position, may extend beyond the receptacle, as is described hereinabove in relation to other embodiments of the invention. The structure on which the pivotal disposing means or tray is pivotally mounted may also provide, in conjunction with a depending arm of the lid, a releasable stop arrangement for defining the opened position of the lid, also as described hereinabove. Furthermore, this said structure may include a guard which lies closely adjacent a rear edge of the pivotal disposing means as it pivots, the arrangement being such that the rear edge of the disposing means clears the guard for disposal of the medical sharps and waste materials into the receptacle from the disposing means when its front edge is proximate the lid. This guard arrangement is particularly efficacious for preventing hand access into the receptacle.

The prevention of hand access as described hereinabove is intended to mean that a person who is using the container to dispose of sharps material, as well as others who may come into contact with the container, cannot extend their hand(s), or portion of their hand(s), into a storage section of the receptacle. This renders the container as a particularly safe storage facility for sharps material substantially eliminating injury or infectious transmission by preventing human contact with that material.

The storage section of the receptacle preferably comprises a substantial portion of the receptacle volume and preferably includes the entire volume of the receptacle save for a section adjacent the opening, in an arrangement in which the pivotal disposing means is disposed within or across the opening. The storage section may also be limited by the storage requirements of the tray within the receptacle when the container is dosed.

The sharps container is preferably lockable to prevent disposal of material therein, such as by unauthorised personnel or when the container is full, and to securely dose the container when it is to be transported to a sharps disposal or destruction facility. While the locking arrangement may take any suitable form, an arrangement has been devised in which two locked positions are available. The first locked position is temporary only in that it is readily releasable. This allows the lid to be reopened easily by releasing the lock. This locking position may be adopted to indicate that the container is not to be used at that time. When it is appropriate for the container to be used, the lock can be moved from the first locked position to the unlocked position easily. The first locked position may also be used when an emptied container is being returned to a hospital or clinic for filling. The second locked position is more permanent, that is, the interengageable locking elements are not readily releaseable. This secures the container against opening without, for example, an appropriate key or combination to unlock the lock, and ensures a container cannot be used as is appropriate for when the container has been filled and is to be transported to a sharps destruction facility.

An embodiment of the invention will now be described, by way of non-limiting example only, with reference to the accompanying drawings.

BRIEF DESCRIPTION OF THE DRAWINGS

FIGS. 8 and 9 illustrate the operation of a foldable tray and its association with the lid of the container of FIG. 1

FIG. 10 shows a tool for use with the container of FIG. 1

DETAILED DESCRIPTION OF PREFERRED EMBODIMENT

Figure 1:
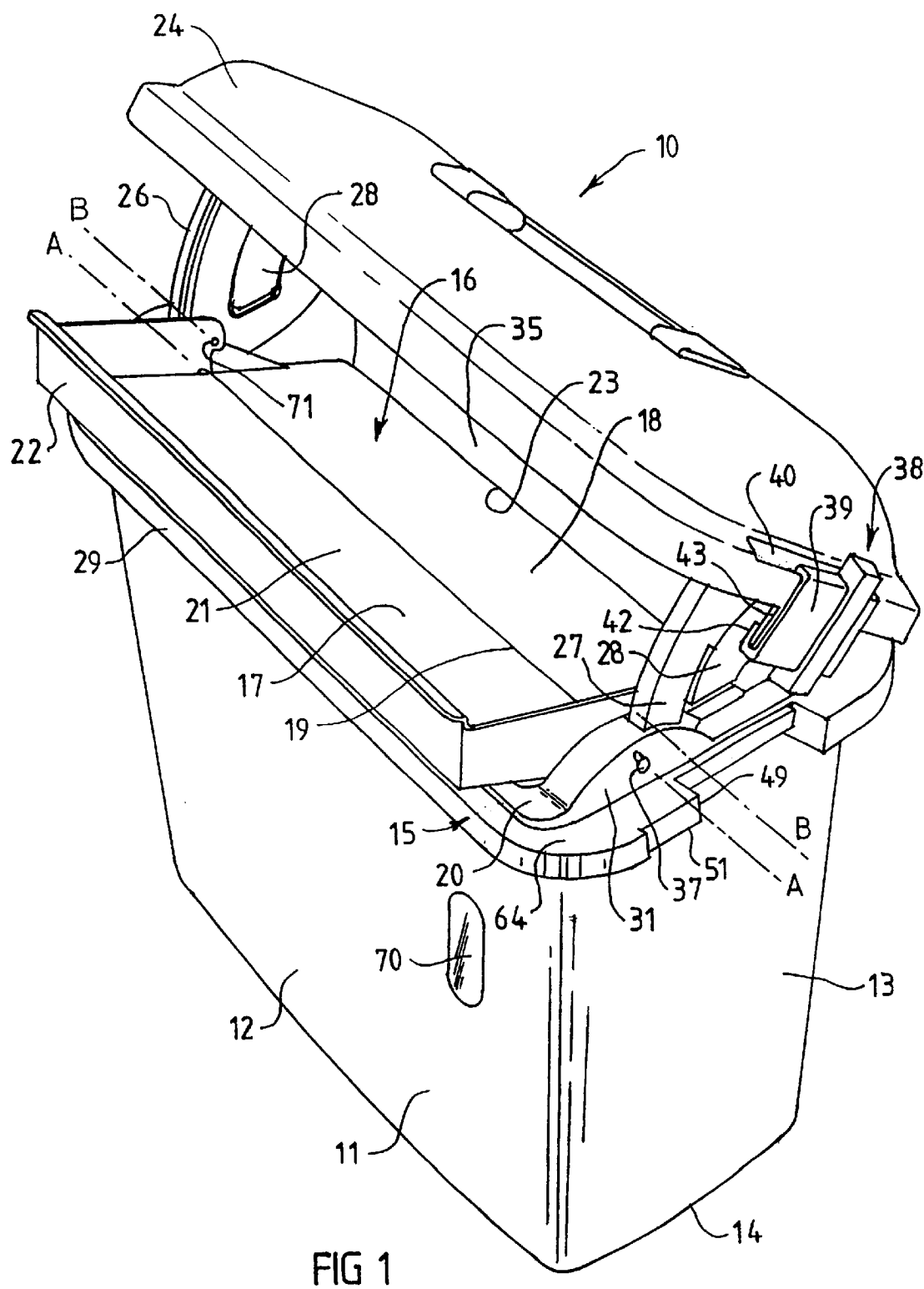
FIG. 1 is a perspective view of a preferred embodiment of a container for medical sharps and other waste materials according to the invention, showing its lid in its opened position.

A reusable sharps container 10 as shown in FIG. 1 includes a receptacle 11 which is generally rectangular in cross-section and in which a front wall 12 and a side wall 13 are visible. The receptacle 11 is closed at a bottom end 14 and is open at a top end which includes a rim 15. Between the rimmed opening and the bottom 14, the receptacle 11 defines a storage section for storing medical sharps and waste materials. The receptacle 11 is slightly tapered from its top end 15 to its bottom end 14 and this facilitates stacking of such receptacles one within another.

Figure 4:
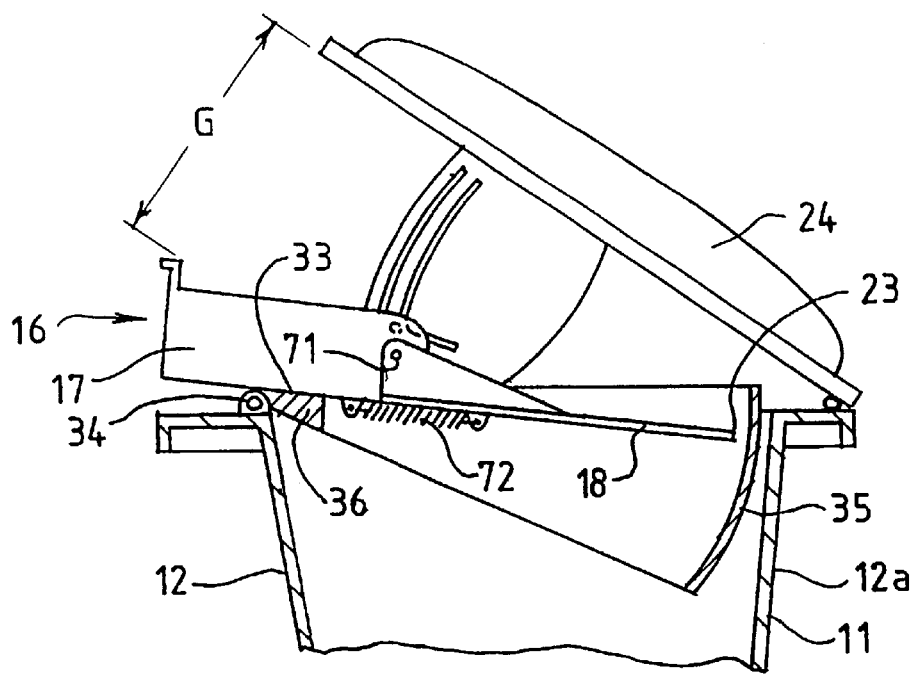
FIGS. 4 and 5 are partial side views, partially sectioned, illustrating pivotal movement of a tray of the FIG. 1 container.
Figure 5:
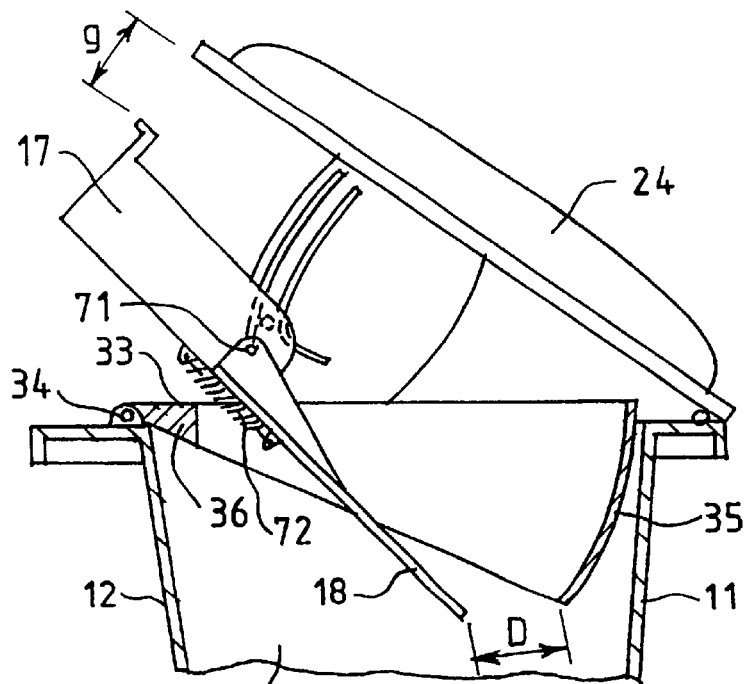

A pivotal disposing means in the form of a tray 16 is pivotably mounted relative to the receptacle 11 at its opening about a pivot axis AA. The tray 16 can pivot from the position shown in FIG. 1, which is a rest position, in a clockwise direction (as viewed in FIG. 1) for the disposal of sharps or waste material to within the receptacle 11. The tray 16 is formed in two parts 17 and 18 which are pivotably connected to each other about a pivot axis BB. The pivot axis BB is formed by a pin extending from one of the tray parts into an opening formed in the other of those parts, on opposite sides of the tray. This is indicated by reference 71. The two parts 17 and 18 are separately formed and in the position shown in FIG. 1, these two parts 17 and 18 abut along an abutment edge 19. Biasing means are attached to the underside of the tray 16 for biasing the two parts 17 and 18 into abutment along the abutment edge 19, in which position the two parts 17 and 18 provide a flat tray surface. The biasing means may be a tensioned coil spring 72 as shown in FIGS. 4 and 5, the ends of which are attached to the underside of the respective tray parts 17 and 18.

The position of the axis AA about which the tray 16 pivots is deliberately made so that the tray 16 tends to rotate due to its weight distribution in an anti Clockwise direction (as viewed in FIG. 1) about that axis, so that when the tray 16 is at rest it is disposed in the position shown in FIG. 1. In that position, the tray 16 rests upon an upper surface 20 of a pivoting structure (to be described hereunder) associated with the rimmed top end 15. Therefore, in the rest position shown in FIG. 1, the tray 16 presents an upper surface 21 upon which medical sharps and waste materials can be placed for disposal into the receptacle 11.

The tray 16 further includes an upright edge wall 22 which extends along the front and side edges of the tray part 17. This edge wall 22 defines a containment area into which a sharps object may be placed and prevents that object from falling from the tray 16, other than across the rear edge 23 of the tray part 18 for disposal into the receptacle 11.

As shown in FIG. 1, the tray 16 is disposed at a slight inclination so that the upper surface 21 of the tray 16 slopes downwardly and into the receptacle 11. This inclined disposition is created by the arrangement of the pivot axis AA at a level slightly below the upper surface 20 upon which the tray 16 rests in the rest position shown in FIG. 1.

The container 10 further includes a closure in the form of a lid 24 which is hingedly connected along a rear edge portion of the rim 15. That hinged connection is not shown in FIG. 1, but is visible in FIG. 2 and is identified by the reference numeral 25. The lid 24 also includes depending arm members 26 and 27 on opposite sides thereof and these arm members assist in guiding the lid 24 to a closed position of the container, as shown in cross-section in FIG. 8. The arm members 26, 27 may be formed separately and attached to the lid 24 by dip arrangements (not shown) on the inside surface of the lid. The arm members 26 and 27 include resiliently biased tabs 28 which are biased away from each other to engage against the upper surface 20 when the lid 24 is in its opened position (as shown in FIG. 1) to stop downward movement of the lid 24 in that position. The arms 26, 27 and tabs 28 in conjunction with surface 20 provide a stop arrangement for defining the opened position of the lid 24. The resiliently biased tabs 28 are easily pressed toward one another to disengage them from the upper surface 20 and allow the lid 24 to be moved from the opened position shown to a closed position. The tabs 28 may be arranged relative to the upper surface 20 and its edges such that downwards pressure on the lid 24 causes the tabs 28 to be cammed inwardly towards each other to disengage them from the surface 20.

The basic operation of the sharps container 10 can now be explained. The sharps container 10 is located in a hospital or medical clinic in an appropriate room or area for the disposal of sharps and waste materials. The container 10 could for example be placed on the ground if it were so constructed to be stable against tipping. Alternatively, a suitable base could be provided for receipt of the container 10. Preferably means is provided on the rear wall of the container for it to be wall mounted. Disposal of a sharps object is a simple and convenient exercise with the sharps object to be disposed of being placed on the tray part 17, after which that object will tend to slide towards the rear edge 23 of the tray 16, by virtue of the inclined disposition of the tray 16. When the object passes the pivot axis AA the tray 16 will tend to pivot about that axis under the weight of the sharps object, in a clockwise direction (as viewed in FIG. 1) causing the object to continue to move towards the rear edge 23 of the tray 16 and ultimately to be deposited within the receptacle 11 when the tray 16 has rotated sufficiently. Having deposited the sharps object within the receptacle 11, the tray 16 pivotally returns under the bias provided by its weight distribution relative to axis M to its rest position as shown in FIG. 1.

The sharps container 10 is advantageous for several reasons. Firstly, the tray 16 provides a broad surface area for the placement of sharps objects thereon. Also, the tray 16 extends slightly forward of a front edge 29 of rim 15 (that is, it protrudes outwardly of the receptacle) and in the opened position of the lid 24, is sufficiently spaced from that lid such that easy access to its broad upper surface 21 is provided.

Secondly, a user of the sharps container 10 simply needs to place a sharps object on the upper tray surface 21 and ordinarily, nothing further of the user will be required, as the inclination of the tray 16 will cause the object to move rearwardly towards the rear edge 23 and once the object has passed the pivoting axis M, the tray 16 will pivot to deposit the object into the receptacle. In some circumstances however, the user may be required to assist the tray 16 to pivot, if the inclination of the tray 16 is not sufficient to cause movement of the object from the first tray part 17 to beyond the pivot axis M. This may occur if the object does not have a tendency to slide relative to the inclined tray 16. Such an object for example might be a flat blade, such as a scalpel or razor blade. In that instance, the user need simply apply a rotating force to the tray 16, for example by pushing on the wall 22 of the front tray part 17.

Figure 2:
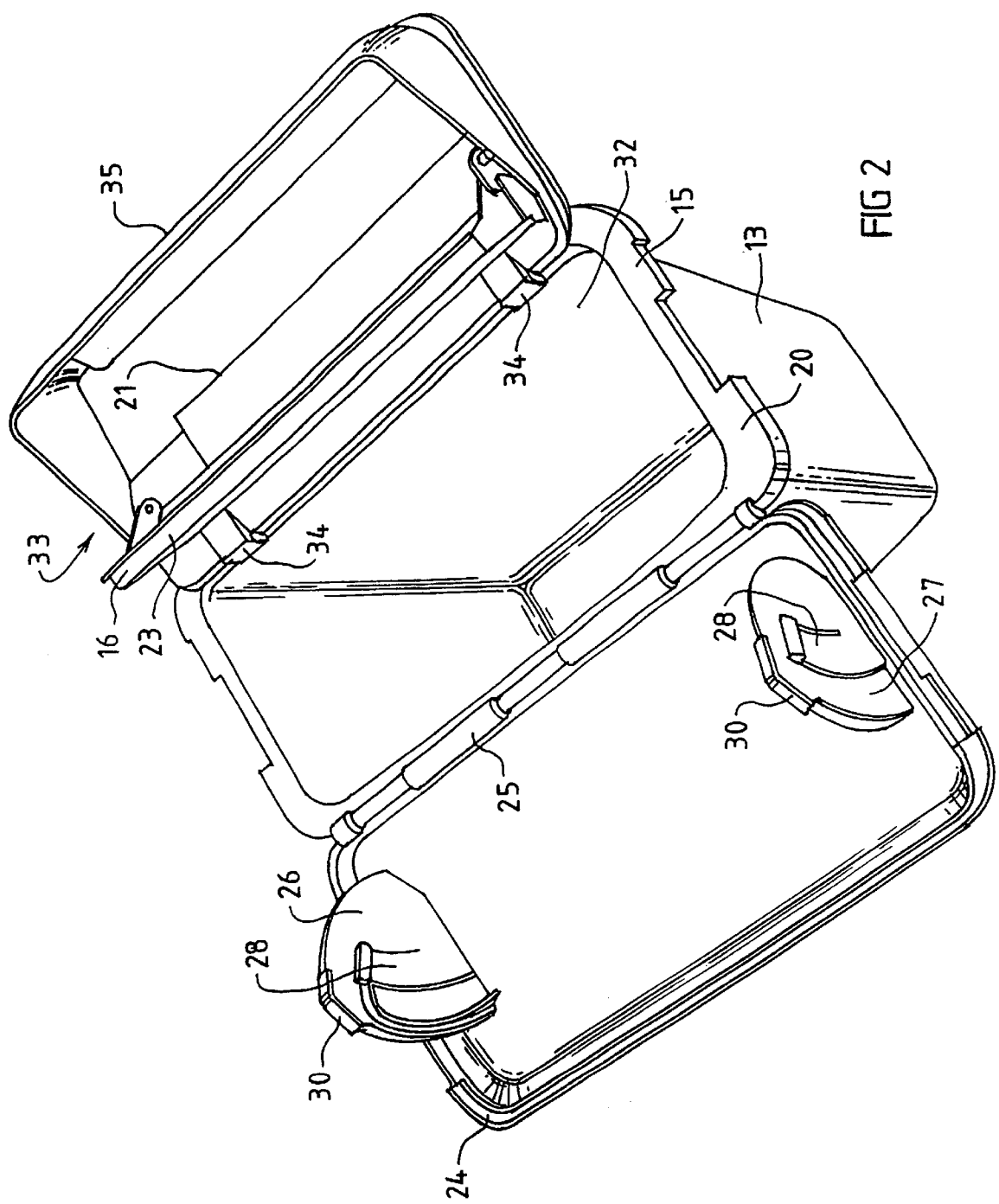
FIG. 2 is another perspective view of the container of FIG. 1, showing its fully opened position for emptying its contents.
Figure 3:
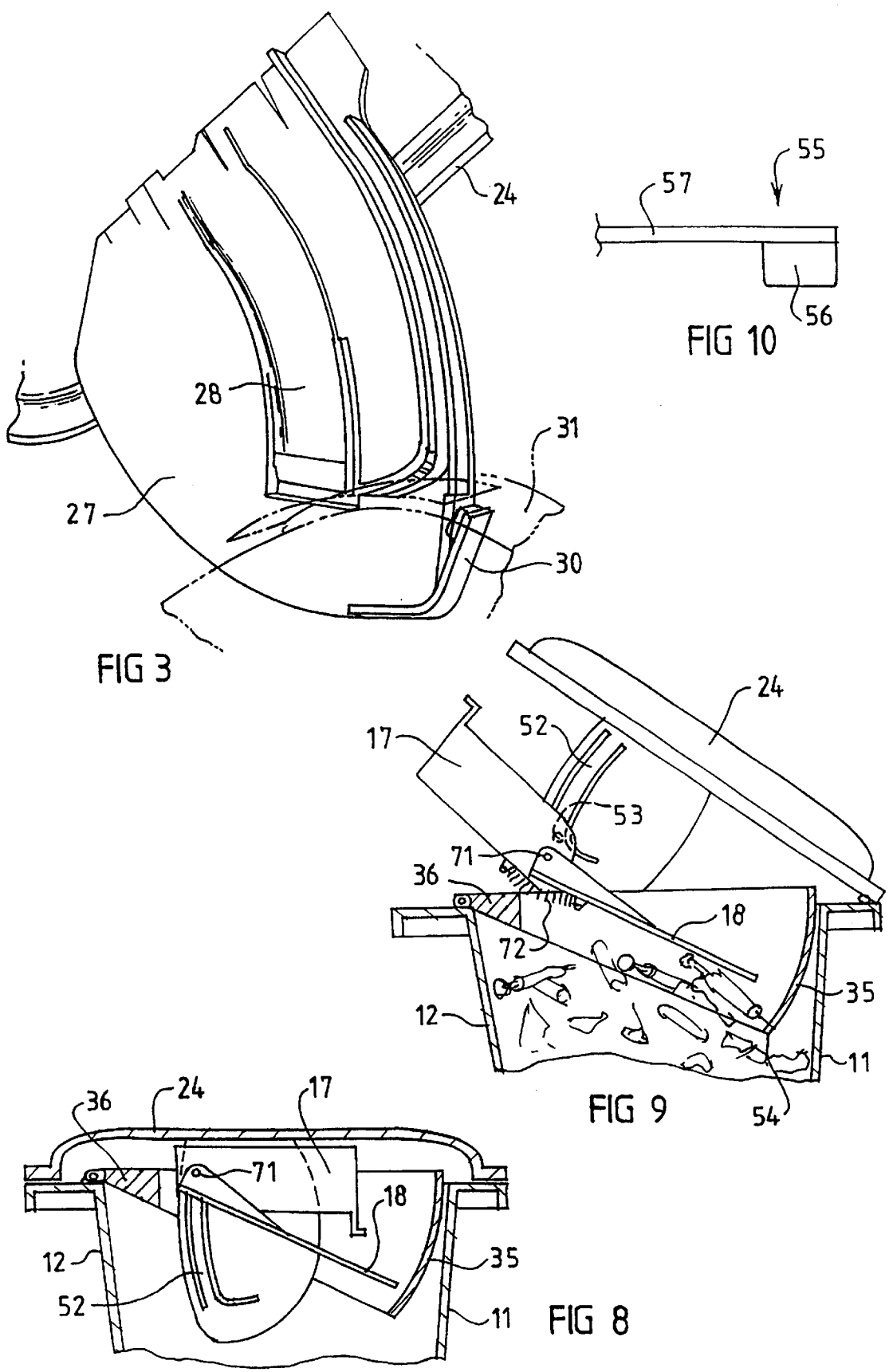
FIG. 3 shows portion of a depending arm of the lid of the FIG. 1 container, illustrating a stop arrangement for defining the opened position of the lid.

The sharps container 10 is shown in FIG. 1 in the opened position of[] the container. That is, the lid 24 is raised at an angle to the point where the resiliently biased tabs 28 move outwardly and engage the upper surface 20 associated with the receptacle to impede return movement of the rid 24 in a downward direction. Further rotation of the lid 24 in an upward direction beyond that shown in FIG. 1 is prevented by a further pair of resiliently biased tabs 30 on arms 26 and 27, as shown in FIGS. 2 and 3. The tabs 30 of arms 26 and 27 engage against the inside surface of a respective protruding part 31 which is associated with the upper surface 20. Thus, the respective pairs of resiliently biased tabs 28 and 30 locate the lid 24 in its opened position shown in FIG. 1, by their engagement with the upper surface 20 and the under surface of the protruding parts 31 respectively, which surfaces are provided by the pivoting structure to be described below. The tabs 30 and protruding parts 31 are further elements of a stop arrangement defining the opened position of the lid 24.

The lid 24 can be moved from the opened position of FIG. 1 to a closed position simply by pressing downwardly on the lid 24 to cam the resiliently biased tabs 28 inwardly so that they are removed from engagement with the upper surface 20, which allows the lid 24 to pivot about its hinged connection 25. The lid 24 can also be caused to pivot beyond its opened position shown in FIG. 1 and this is principally required for emptying the container 10. As shown in FIG. 2 the lid 24 can be fully opened away from the opening 32 to facilitate emptying of the contents of the receptacle 11 without hindrance from the lid 24. Movement of the lid 24 from the position shown in FIG. 1 to that shown in FIG. 2 requires displacement of the resiliently biased tabs 30 from engagement with the inside surface of the protruding parts 31. Displacement of the resiliently biased tabs 30 can be made by any suitable means, and in FIG. 1 an opening 37 in an outer side wall of each protruding part 31 is provided for receiving a special tool which can facilitate the displacing movement. The tool can form part of an automated machine designed to empty the container 10, or it can be provided for manual operation. The tool is one which can fit within the opening 37 which is of a specific shape for receiving a complementary shaped key or tool. The opening 37 is shown to have a somewhat keyhole configuration, but it may have any suitable form to receive a relevant tool or key. This arrangement prevents displacement of the resiliently biased tabs 30 by unauthorised personnel who do not possess the relevant tool or key.

The opening 37 is provided in the side wall of each protruding part 31, which wall is disposed substantially perpendicularly to the direction in which the tabs 30 are displaced to facilitate movement of the lid 24 to the emptying position of FIG. 2. The tool or key provided to displace the tabs 30 can be of a form shown in FIG. 10. This tool 55 includes an operative bit 56 fixed to an elongate shaft 57. The bit 56 is inserted through the opening 37, whereafter the shaft 57 is rotated to bring the bit 56 into displacing engagement with the tab 30. If the tool 55 is manually operable, the end of the shaft 57 remote from the bit 56 can be fitted with a handle or finger grip while if it is part of automated machinery, it can be fixed thereto in any suitable manner.

The container 10 also includes a pivoting structure 33 (see FIG. 2) which is pivotally connected to the top rim 15 of the receptacle 11 by a hinged connection 34 opposite the hinged connection 25 of lid 24. The pivoting structure 33 provides the upper surface 20 and the protruding parts 31. The pivoting structure 33 includes the tray 16 which is pivotally connected thereto, and further includes an arcuate guard member 35 which, in the FIG. 1 illustration, with the pivoting structure 33 in its seated position or rim 15, lies adjacent the rear edge 23 of the tray 16. The hinged connection 34 is such that pivoting structure 33 may be completely removed from receptacle 11 if desired. Structure 33 also includes dips (not shown) on its side opposite the hinged connection 34 for latching the pivoting structure 33 to the receptacle 11 in its seated position thereon. The lid 24 and the pivoting structure 33 are released and opened, in turn. That is, first the resiliently biased tabs 30 are displaced and the lid 24 is then pivoted to the fully open position of FIG. 2, the pivoting structure 33 can then be pivoted to a fully open position (also shown in FIG. 2) so that the receptacle opening 32 is exposed. Reassembly of the sharps container 10 is conducted in the reverse manner.

As can be seen from FIG. 2, the pivoting structure 33 can be pivoted to fully expose the receptacle opening 32 so that emptying of the receptacle 11 is not hindered by that structure. The sharps container 10 as illustrated is particularly useful, in that it may be emptied automatically by automated machinery. The advantage here is that workers who may be charged will emptying the sharps container might be exposed to risk of injury unless the emptying procedure is carried out in a very safe manner. For example it would not be acceptable for a worker to grip the receptacle 11 on either side of top end 15 because the workers fingers could project into the receptacle 11, and will expose the worker to the sharps material contained therein, with the potential for needle stick or other injuries as discussed earlier. It is envisaged that machinery may be employed so that a closed container is automatically opened to the condition shown FIG. 2 and inverted to release the contents without any risk to the operator of that machinery.

The curve of the guard member 35 of pivoting structure 33 is substantially the same as the curved path of the rear edge 23 of tray 16 and the guard 35 acts to prevent a gap from forming behind the rear edge 23 as the tray 16 pivots, so as to prevent access to within the receptacle 11 during pivoting movement of the tray 16. The arrangement is better illustrated in FIGS. 4 and 5 which show pivoting movement of the tray 16 from the rest position of FIG. 1 to a disposing position. In these figures, it can also be seen that the pivoting structure 33 includes a front guard member 36 which acts in the same manner as the arcuate guard member 35 to prevent gaps forming during pivoting movement of the tray 16. The guard member 36 blocks the gap formed between the underneath of the tray 16 and the front surface 12.

As shown in FIG. 4, a gap "G" between the front edges of the lid 24 and the tray 16 in its opened position, is sufficient to allow a sharps object to be easily placed on the tray 16. However, the gap G is also sufficient to allow a user to place his/her hand and arm into the container and therefore it is necessary that means be provided to prevent access to within the receptacle where disposed sharps and waste materials may be located. The guard 35 provides such a means. In the FIG. 4 arrangement, the space between the rear wall 12a of the receptacle 11 is small, but within that space is disposed a portion of the guard member 35 which lies closely adjacent to the path of the rear edge 23 of tray 16. Thus, while the gap between the rear edge 23 and the rear wall 12a will increase upon rotation of the tray 16, the guard 35 prevents access to within the receptacle by blocking that gap.

The extent of the guard 35 is limited, as an opening is required for actual disposal of sharps objects and waste materials into the receptacle from tray 16. The disposal opening D is shown in FIG. 5. At this disposal position, it is shown that the gap "G" has diminished to a much smaller gap "g" which is not sufficient for a user's hand or arm to be inserted therethrough and therefore access to within the receptacle 11 through the opening D is prevented.

Thus, as illustrated by FIG. 4, the container 10 has a large access opening, as indicated by the dimension G and depending upon the degree to which lid 24 is opened relative to receptacle 11, whilst ensuring that hand access to within the receptacle 11 is prevented. In its opened position, the lid 24 may extend at an angle of about 40° or greater to the receptacle's upper rim surface. The invention allows an access opening G of the order of, for example, 80 mm to be realised as against prior art sharps containers having openings typically of the order of 50 mm. The provision of such a large access opening enabled by the invention together with a width dimension of, for example, 300 mm for tray 16, allows relatively large medical sharps and waste materials, for example such as a metering intravenous "giving set", to be disposed of within the container 10. Furthermore, a large access opening allows a person to dispose of sharps into the container 10 directly from a tray such as, for example, a kidney dish, onto which the sharps may be placed immediately after use. That is, such a dish is simply carried to the container 10 and manipulated to tip the sharps therefrom onto pivotal tray 16, thereby avoiding any actual handling of the sharps after their placement on the kidney dish.

Figure 6:
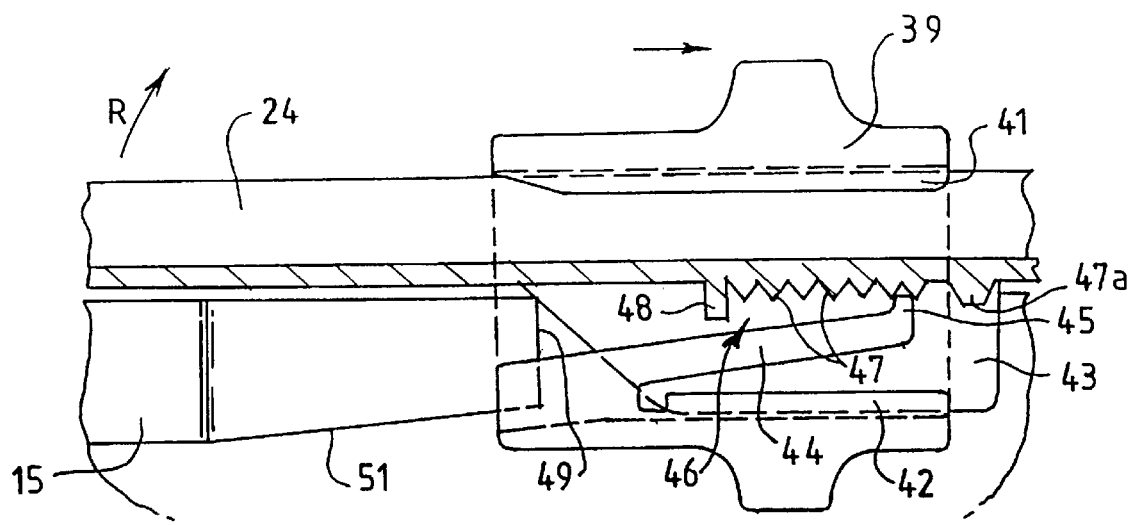
FIGS. 6 and 7 illustrate a locking arrangement for the lid of the container of FIG. 1.
Figure 7:
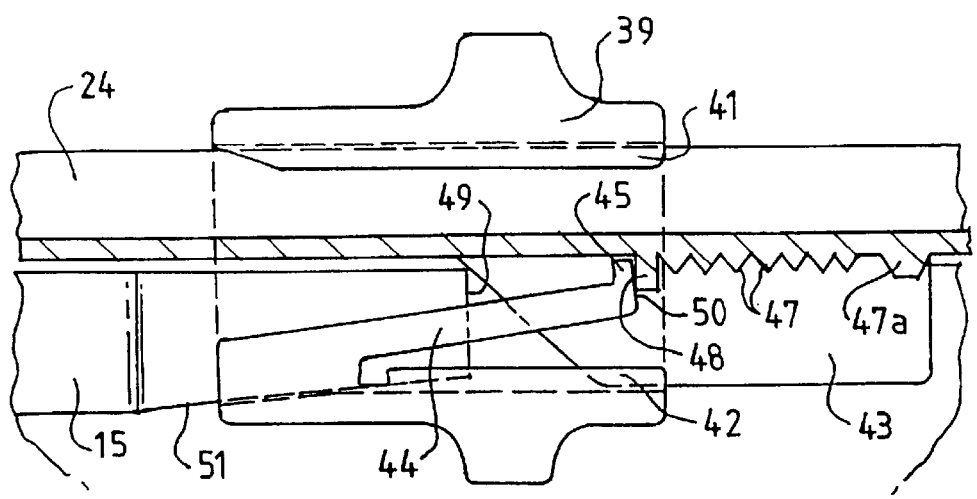

The sharps container 10 contains locking means for locking the lid 24 in a closed position relative to the receptacle 11. The locking means is illustrated in FIG. 1 in the form of a sliding lock arrangement 38 which is shown in more detail in FIGS. 6 and 7. There is a sliding lock 38 on opposite sides of the container 10. Each sliding lock arrangement 38 includes a sliding member 39 which is permanently attached to the lid 24 by way of a leg section 41 which extends into a channel 40 in the lid 24 (FIG. 1) and a further leg section 42 which extends about a planar member 43 which depends from the lid 24. Extending from the leg section 42, is a resilient latching member 44. The latching member 44 is integrally formed with the leg section 42 and includes an engagement end portion 45. The end portion 45 is arranged to be engagable with a rack 46 that comprises projections 47 and an end projection 48. As illustrated in FIGS. 6 and 7, the projections 47 are generally triangular, having sloping sides, the first one 47a of which is larger than the others, and the projection 48 has sides that extend substantially normally from an undersurface of the lid's rim. The end portion 45 is arranged to engage the projections 47 and projection 48 to either temporarily or permanently lock the lid 24 to the receptacle 11. The mechanism of the lock arrangement 38 will now be described.

Referring first to FIG. 6, the sliding member 39 is shown with the end portion 45 engaged between the inclined projections 47. Engagement of the end portion 45 in this position has been achieved by sliding movement of the sliding member 39 in a direction towards the left as shown in FIG. 6, with this leftwise movement, the latching member 44 has resiliently flexed to enable the end portion 45 to ride over the rightmost projection 47a so as to come to rest along the projections 47. In this position the sliding member 39 engages over an end portion 49 of a cut-out in the rim 15 of the receptacle 11 and the lid 24 is therefore held against rotation in the direction R by that engagement and is therefore latched closed. However, the sliding member 39 can be moved to the right, as the inclined projections 47 allow the end portion 45 to slide thereover so as to disengage the sliding member 39 from the end portion 49. In the latched position of the sliding member 39 shown in FIG. 6, the container lid 24 is prevented from opening, but any person can move the sliding member 39 to the right so that the lid 24 can be opened. In this position therefore, the sliding member latches the lid 24 closed but does not lock or secure it against reopening.

In FIG. 7, the sliding member 39 has been moved to the left, so that the end portion 45 of the latching member 44 is moved over the projection 48. This leftward movement is facilitated by the end portion 45 riding over the inclined projections 47 and the vertical projection 48. Movement of the sliding member 39 to the right is now prevented, as an upright edge 50 of the end portion 45 abuts substantially squarely against the normal projection 48, so that the end portion 45 cannot ride over the projection 48 against which it abuts. In this position of the sliding member 39, the lid 24 is permanently locked to the receptacle 11 and opening of the lid 24 is not possible. The container 10 can be transported to an emptying facility in this locked condition.

Release of the sliding member 39 can be made by a further special tool which is inserted into the sliding member 39 to depress the latching member 44 and release its end portion 45 from engagement with the vertical projection 48. Any suitable tool can be provided for this purpose.

It will be noted that in FIGS. 6 and 7 an inclined ramp section 51 is provided on the rim 15 of the receptacle 11 which tapers away from the end portion 49 of the cut-out The purpose of this ramp section 51 is to firmly close the lid 24 relative to the receptacle 11 when the sliding member 39 is slid into a permanently locked position. By virtue of the ramp 51, the sliding member 39 applies a progressively increasing closing force, so that the contents of the container are secured therein. It is noted that in FIG. 7, the end portion 45 is located past vertical projection 48, but it is possible for the sliding member to be slid further left for the sliding member 39 to creep further up the ramp section 51 and apply a greater closing force between the lid 24 and the receptacle 11.

Folding of the tray 16 on moving the lid 24 to a closed position is shown in FIG. 8 of the drawings. In this figure, it can be seen that the tray part 17 is folded over and is located within the container 10 adjacent the lid 24. The other tray part 18 is disposed at an angle to the tray part 17 and that angle is dictated somewhat by the level of sharps material in the container. The arrangement of FIG. 8 illustrates that the tray 16 can be fully retained in an inoperative condition within the container 10 when the container is closed, and can be transported in that position to the facility at which the container is emptied. Thus, separation of the tray from the container is unnecessary so that loss of the tray is unlikely to happen.

The tray 16 is rotated to the position shown in FIG. 8 by cam and follower arrangements disposed on the insides of the arm members 26 and 27 and on the side edges of the edge wall 22 of tray part 17. The cam arrangement may be a cam track as can be seen in the various figures and is identified by the reference numeral 52 in FIG. 8. The cam follower may be a pin, which engages in the cam track 52, as is shown in dot outline in FIG. 9 and is identified by the reference numeral 53. Each cam follower 53 is fixed to tray part 17. The arrangement of each cam 52 and cam follower 53 is such that, as the lid 24 is moved from the opened position of FIG. 9 to the closed position of FIG. 8, the cam follower 53 engages within the cam 52 and that causes rotation of the tray part 17 to the position shown in FIG. 8. The tray part 18 moves with the tray part 17 until the tray part 18 pivots relative to the tray part 17 as may eventually occur depending on when the tray part 18 is prevented from further movement with the tray part 17. That is, the final disposition of the tray part 18 is not fully determined by the cam and follower arrangement. As shown in FIG. 9, the position of the tray part 18 is somewhat dependant upon the amount of sharps material contained in the receptacle 11 and when the receptacle 11 is filled, the tray part 18 in the closed position of the lid 24 will rest against the top of that material. However, if the container is less full, the tray part 18 may rest on or adjacent the front wall 12 if there are no sharps materials to prevent its movement to that position.

On opening the lid 24, the cam and follower arrangements 52, 53 are operative to move the tray 16 from its inoperative condition to an operative condition, and in its operative condition the tray 16 moves to is normal rest position (see FIG. 1) under its overbalance bias. The cam 52 and follower 53 arrangement of FIGS. 8 and 9 is shown in schematic detail only. That arrangement could take a variety of forms and therefore the specific contour is not important. However, it should be noted for the embodiment illustrated that during closing movement of the lid 24, the undersurface of the tray 16 remains closely adjacent to the front guard member 36 to prevent hand access to within the receptacle from underneath the tray 16.

In the closed position of the lid 24, a seal (not shown), which is fixed to the edge of the lid 24, engages against an upper surface 64 of the rim 15 of the receptacle 11, adjacent to and outside of the pivoting structure 33. The seal can be accommodated in a channel extending about the periphery of the lid 24 or it can be otherwise fixed to the lid. Alternatively a seat could be fixed to the surface 64.

As can be seen from FIG. 9, engagement of the tray part 18 with the sharps and waste materials contained in the receptacle 11 provides an indication that the container 10 is full. When the container 10 reaches its capacity, the tray part 18 will not be able to pivot past the bottom edge 54 of the guard member 35 and any sharps material placed in the tray will not enter the storage section of the receptacle. That does not present any difficulties, as the container 10 can then be closed and locked for transport to a disposal facility.

The described structure also provides a further advantage in terms of safety in that when the receptacle 11 is substantially full, a sharps object placed on tray 16 for disposal commonly becomes jammed between the rear edge 23 of tray 16 and the bottom edge 54 of guard 35, which prevents tray 16 from pivotally returning to its rest position. Thus the tray 16 is no longer accessible for sharps and waste materials to be placed thereon. This feature prevents the container 10 from being overfilled.

Preferably the receptacle 11 includes a window 70 (see FIG. 1) to allow the level of sharps and waste materials in the container 10 to be observed. The window 70 may include a mark for indicating that the receptacle is full.

The container 10 may also include an additional latch (not shown) operative between the lid 24 and the rim 15 of the receptacle 11 for providing additional security against misadventure in transporting a full container to a disposal facility. Such a latch may be centrally located on the front of the lid 24 and receptacle 11 to provide added security against the lid becoming accidentally opened if the full container 10 is, for example, dropped.

Figure 11:
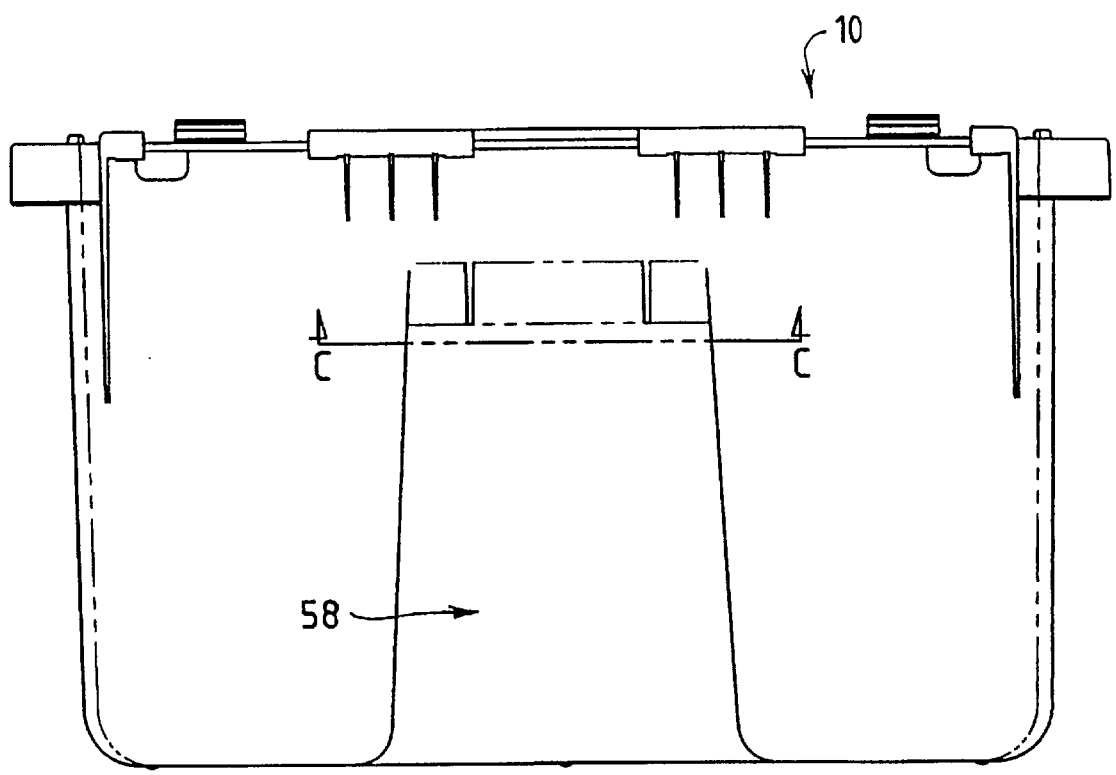
FIGS. 11 and 12 show portions of the container of FIG. 1 providing for the mounting of the container on a wall.
Figure 12:
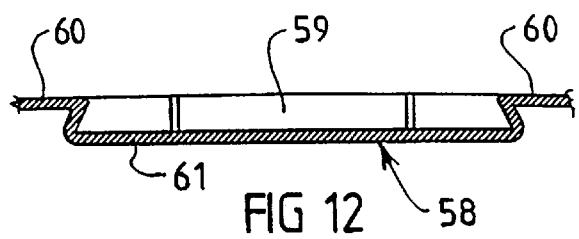
Figure 13:
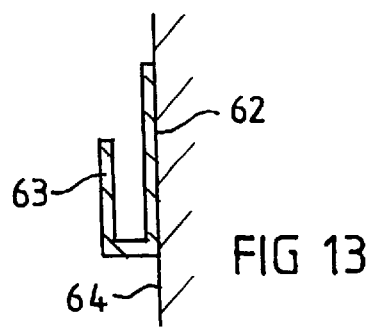
FIG. 13 shows a wall bracket on which the container of FIG. 1 may be mounted.

The container 10 may be wall mounted and an example embodiment of an arrangement for that purpose is shown in FIGS. 11 and 12. FIG. 11 is a rear view of the container 10 and the wall mounting arrangement 58 is central of the rear of the container. A cross-sectional view of the mounting arrangement through line C—C of FIG. 11 is shown in FIG. 12 and this shows that the mounting arrangement 58 defines a channel 59 which extends from a rear surface 60 of the container 10 to a base 61 of the arrangement 58. The channel 59 is provided to receive an upstanding section 63 of a mounting bracket 62 such as shown in FIG. 13, which figure shows the bracket 62 in cross-section fixed in any suitable manner to a wall 64. A dove-tailed shape for the channel 59 sides facilitates secure support of the container 10 by the bracket 62 as the side edges of the bracket section 63 can be made to firmly fit into the dove-tailed sides of the channel 59.

A container according to the invention can be manufactured from any suitable material or combination of materials, but preferably is manufactured from plastic materials. Alternatively, metallic materials may be used, or a combination of plastic or metallic materials. Manufacture of the container can be by any suitable method, such as by injection or rotational plastic moulding, or by plastic fabrication. Metallic components could for example be pressed or stamped. The choice of material and of manufacturing processes is a choice within the knowledge of a person skilled in this art. Clearly, for a reusable container, the material of manufacture and method of manufacture must be compatible with its reuse and sanifization or sterilization requirements.

The invention described herein is susceptible to variations, modifications and/or additions other than those specifically described and it is to be understood that the invention includes all such variations, modifications and/or additions which fall within the scope of the following claims.

What is claimed is:

1. A container comprising a receptacle for receiving and storing medical sharps and waste materials, the receptacle having an opening, a lid for closing the opening, the lid being hinged to the receptacle for movement between opened and closed positions, a pivotal disposing member mounted at the opening wherein the lid and the pivotal disposing member are operatively associated such that the movement of the lid from its closed to its opened position moves the disposing member from an inoperative condition to an operative condition wherein it is accessible for medical sharps and waste materials to be placed thereon, the disposing member being pivotally moveable independently of the lid for disposal of the medical sharps and waste materials therefrom into the receptacle, and wherein the disposing member is arranged relative to the lid in its opened position, and to the receptacle, to prevent hand access into the receptacle for all positions of the disposing member about its pivotal axis.

2. A container as claimed in claim 1 wherein the pivotal disposing member is a tray which is biased to return to a rest position for the opened position of the lid wherein it is accessible for medical sharps and waste materials to be placed thereon.

3. A container as claimed in claim 1 or claim 2 including a guard associated with the receptacle, wherein the disposing member is arranged such that as it pivots a front edge thereof moves towards the opened lid and a rear edge thereof moves closely adjacent the guard, wherein said rear edge clears the guard for disposal of medical sharps and waste materials into the receptacle from the disposing member when said front edge is proximate said lid and whereby the pivotal disposing member is prevented from returning to an accessible position when the receptacle is substantially full by the lodgment of an object for disposal between its rear edge and the guard.

4. A container as claimed in claim 1 wherein the pivotal disposing member is a tray which in its operative condition is biased to return to a rest position from its disposal position.

5. A container as claimed in claim 4 wherein the tray at said rest position is inclined towards the receptacle interior to facilitate the sliding of sharps objects placed thereon access the tray and thereby promote pivoting of the tray from its rest position to its disposal position.

6. A container as claimed in claim 4 wherein a portion of the tray in its rest position protrudes outwardly beyond the receptacle to facilitate placement of medical sharps and waste materials thereon.

7. A container as claimed in claim 4 or 5 for wherein the tray is foldable for storage within the container when in its inoperative condition.

8. A container as claimed in any one claims 4 to 6 wherein the lid includes a depending arm and the receptacle includes a structure for engaging the arm, wherein the arm and said structure provide a stop arrangement for defining the opened position of the lid, wherein the arm and the tray included a cam and follower arrangement providing said operative association of the lid and the tray.

9. A container as claimed in claim 8 wherein the arm includes a cam track and the tray includes a follower in the form of a pin engaged with the cam track.

10. A container as claim in claim 8 wherein said structure includes a guard and wherein the tray is arranged such that as it pivots a front edge thereof moves towards the opened lid and a rear edge thereof moves closely adjacent the guard, wherein said rear edge clears said guard for disposal of medical sharps and waste materials into the receptacle from the tray when said front edge is proximate said lid.

11. A container as claimed in claim 8 wherein the tray is pivotally mounted on said structure and said structure is removably attached to the receptacle, wherein said stop arrangement is releasable for the lid to be moved beyond its opened position and said structure is moveable relative to the receptacle to uncover said opening for the container to be emptied by inverting the receptacle.

12. A container as claimed in claim 11 wherein said structure is removably hinged to the receptacle opposite the hinged connection of the lid to the receptacle.

13. A container as claimed in claim 1 including a structure on which the pivotal disposing means is pivotally mounted, said structure being removably attached to the receptacle and moveable relative thereto for moving the pivotal disposing means away from the receptacle opening, wherein the closure is a lid and the lid is moveable beyond its opened position to completely uncover the receptacle opening whereby the container can be emptied of its contents by inverting the receptacle.

14. A container as claimed in claim 13 wherein the pivotal disposing member is a tray which is foldable and is stored within the container when the lid is in its closed position.

15. A container as claimed in claim 14 wherein the tray is biased to move to a rest position upon the lid being moved to its opened position, the tray being accessible at its rest position for medical sharps and waste materials to be placed thereon.

16. A container as claimed in claim 15 wherein at the rest position for the tray, a portion thereof protrudes outwardly beyond the receptacle to facilitate placement of medical sharps and waste materials thereon.

17. A container as claimed in claim 16 wherein at the rest position for the tray, the tray is inclined towards the receptacle interior to facilitate a sharps object placed thereon sliding across it to promote pivoting of the tray from its rest position to a disposal position.

18. A container as claimed in claim 1 wherein the receptacle and the lid include interengageable locking elements for locking the lid in its closed position to the receptacle.

19. A container as claimed in claim 18 wherein the locking elements define two locked positions, a first one of which is readily releasable and the second of which is not readily releaseable, wherein said first locked position is for use when the container is not full and said second locked position is for use when the container is full.

20. A container is claimed in claim 19 wherein said second locked position is releasable by use of a tool.

21. A container for storing medical sharps and waste materials comprising
a receptacle having an opening at the top thereof,
a movable lid for completely closing the opening, the lid being hinged to the receptacle for movement between opened and closed positions,
a pivotal tray disposed at the opening and mounted to be accessible for medical sharps and waste materials to be placed thereon when the lid is in its opened position, and the tray being pivotally movable with respect to the opening of the receptacle for disposal of medical sharps and waste materials therefrom into the receptacle, the tray being arranged to extend outwardly from the opening when the lid is in the opened position, the tray being arranged relative to the lid in its opened position and arranged relative to the receptacle and its opening to prevent hand access into the receptacle for all positions of the tray about its pivotal axis.

22. A container as in claim 21 wherein the mounting for the tray is arranged to cause it to extend outwardly from the opening in the receptacle when the lid is in its opened position, and to be fully retracted into the container when the lid is in its closed position.

23. A container comprising a receptacle for receiving and storing medical sharps and waste, the receptacle having an opening,
a lid for closing the opening hingedly connected to the receptacle and manually movable between opened and closed positions,
a disposing tray for medical sharps and waste pivotally mounted at the receptacle opening such that the lid and the tray are operatively associated so that the movement of the lid from its closed to its opened position moves the tray from an inoperative condition to an operative condition wherein the tray is accessible for medical sharps and waste materials to be placed thereon and in the opened position of the lid the disposing tray impedes hand access into the receptacle through said opening, and
the disposing tray being pivotally movable such that the medical sharps and waste are disposable therefrom into the receptacle from a rear portion of the disposing tray whereby said front portion of the tray moves towards said lid to continue to impede hand access into the receptacle.

24. A container as claimed in claim 23 wherein the disposing tray is movable from a stored position, in dependence upon movement of the lid from its closed to its opened positions, to a block position at said receptacle opening to thereby impede hand access into the receptacle.

25. A container as claimed in claim 23 or 24 wherein the disposing tray is pivotally movable independently of the lid for the medical sharps and waste to be disposed therefrom into the receptacle from said rear portion of the disposing tray.

26. A container comprising a receptacle for receiving and storing medical sharps and waste, the receptacle having an opening,
a lid for closing the opening hingedly connected to the receptacle and manually movable between opened and closed positions,
a disposing tray mounted at the opening wherein for the opened position of the lid, the disposing tray is accessible for medical sharps and waste materials to be placed thereon, the lid and the tray are operatively associated so that the movement of the lid from its closed to its opened position moves the tray from an inoperative condition to an operative condition wherein the tray is accessible for medical sharps and waste materials to be placed thereon, the disposing tray being pivotally movable independently of the closure for disposal of the medical sharps and waste materials therefrom into the receptacle, and a structure hingedly connected to the receptacle and on which the disposing tray is pivotally mounted to be disposed at the receptacle opening, the structure being movable relative to the receptacle to move the disposing tray away from the receptacle opening to facilitate emptying of the container.

27. A container as claimed in claim 26 wherein the lid and the disposing tray are hingedly connected to the receptacle along opposite edges of said receptacle opening.

28. A container comprising a receptacle for receiving and storing medical sharps and waste materials, the receptacle having an opening, a lid for closing the opening hingedly connected to the receptacle and manually movable between opened and closed positions, the opened position being defined by a stop structure acting between the lid and the receptacle and which is releasable for the lid to be opened beyond its opened position, a disposing tray for medical sharps and waste pivotally mounted at the receptacle opening such that for the opened position of the lid the lid and the tray are operatively associated so that the movement of the lid from its closed to its opened position moves the tray from an inoperative condition to an operative condition wherein the tray is accessible for medical sharps and waste materials to be placed thereon and the disposing tray impedes hand access into the receptacle through said opening, the disposing tray being pivotally movable for medical sharps and waste placed thereon to be disposed therefrom into the receptacle, wherein the pivotal mounting of the disposing tray provides for manual removal of the disposing tray away from the receptacle opening, and whereby the lid is openable beyond its opened position and the disposing tray is removable away from the receptacle opening to facilitate emptying of the receptacle.

29. A container comprising a receptacle for receiving and storing medical sharps and waste materials, the receptacle having an opening, a lid for closing the opening, the lid being hinged to the receptacle for movement between opened and closed positions, a pivotal disposing member comprising a tray mounted at the opening wherein for the opened position of the lid, the tray is accessible for medical sharps and waste materials to be placed thereon, the tray being pivotally movable for disposal of the medical sharps and waste materials therefrom into the receptacle, the tray being arranged relative to the lid in its opened position, and the receptacle, to prevent hand access into the receptacle for all positions of the tray about its pivotal axis, and the lid and the tray are operatively associated such that the movement of the lid from its closed to its opened position moves the tray from an inoperative condition to an operative condition wherein it is accessible for medical sharps and waste materials to be placed thereon, the tray in its operative condition being biased to returned to a rest position from its disposal position, and the tray at said rest position being inclined towards the receptacle interior to facilitate the sliding of sharp objects placed thereon access the tray and thereby promote pivoting of the tray from its rest position to its disposal position, a portion of the tray in its rest position protrudes outwardly beyond the receptacle to facilitate placement of medical sharps and waste materials thereon, and the tray being foldable for storage within the container when in its inoperative condition.

30. A container comprising a receptacle for receiving and storing medical sharps and waste materials, the receptacle having an opening, a closure for closing the opening, the closure being hinged to the receptacle for movement between opened and closed positions, a pivotal disposing member mounted at the opening wherein for the opened position of the closure, the disposing member is accessible for medical sharps and waste materials to be placed thereon, the disposing means being pivotally moveable for disposal of the medical sharps and waste materials therefrom into the receptacle, wherein the disposing member is arranged relative to the closure in its opened position, and the receptacle, to prevent hand access into the receptacle for all positions for the disposing member about its pivotal axis, and a structure on which the pivotal disposing member is pivotally mounted, said structure being removably attached to the receptacle and moveable relative thereto for moving the pivotal disposing member away from the receptacle opening, wherein the closure is a lid and the lid is moveable beyond its opened position to completely uncover the receptacle opening whereby the container can be emptied of its contents by inverting the receptacle.

* * * * *

UNITED STATES PATENT AND TRADEMARK OFFICE
CERTIFICATE OF CORRECTION

PATENT NO. : 6,250,465 B1  Page 1 of 1
APPLICATION NO. : 09/463045
DATED : June 26, 2001
INVENTOR(S) : Daniels et al.

It is certified that error appears in the above-identified patent and that said Letters Patent is hereby corrected as shown below:

On the Title Page Item (73) please correct the Assignee as follows;

Please replace "Catalina Nominees Pty. Ltd." with --Catilina Nominees Pty. Ltd.--.

Signed and Sealed this

Second Day of December, 2008

JON W. DUDAS
*Director of the United States Patent and Trademark Office*